US012781599B2

(12) United States Patent
Patel

(10) Patent No.: US 12,781,599 B2
(45) Date of Patent: Nov. 3, 2026

(54) MOVABLE MOUNT FOR WELL CELLAR GAS DETECTORS

(71) Applicant: SAUDI ARABIAN OIL COMPANY, Dhahran (SA)

(72) Inventor: Pareshkumar L. Patel, Al Khobar (SA)

(73) Assignee: SAUDI ARABIAN OIL COMPANY, Dhahran (SA)

(*) Notice: Subject to any disclaimer, the term of this patent is extended or adjusted under 35 U.S.C. 154(b) by 594 days.

(21) Appl. No.: 18/360,127

(22) Filed: Jul. 27, 2023

(65) Prior Publication Data

US 2025/0034970 A1 Jan. 30, 2025

(51) Int. Cl.
*E21B 41/00* (2006.01)
*G01N 33/00* (2006.01)

(52) U.S. Cl.
CPC ..... *E21B 41/0021* (2013.01); *G01N 33/0044* (2013.01)

(58) Field of Classification Search
CPC ........................ E21B 41/0021; G01N 33/0044
USPC .......................................................... 166/342
See application file for complete search history.

(56) References Cited

U.S. PATENT DOCUMENTS 8,127,837 B1 * 3/2012 Rose ....................... E21B 33/02 405/52
8,362,905 B2 * 1/2013 Lohmann ............. G01N 27/286 73/866.5
9,085,961 B2 * 7/2015 Ehalt .................. E21B 41/0021
11,340,203 B2 5/2022 Su et al.
12,529,687 B1 * 1/2026 Kliethermes ...... G01N 33/0075
(Continued)

FOREIGN PATENT DOCUMENTS

CN 209959234 U 1/2020
CN 212207293 U 12/2020
(Continued)

OTHER PUBLICATIONS

Occupational Safety and Health for Oil and Gas Well Drilling and Servicing Operations; API Recommended Practice 54, Fourth Edition, Feb. 2019 (Year: 2019).*
(Continued)

*Primary Examiner* — Tara Schimpf
*Assistant Examiner* — Patrick F Lambe
(74) *Attorney, Agent, or Firm* — Osha Bergman Watanabe & Burton LLP

(57) ABSTRACT

An apparatus for a cellar of a well includes a first track, a first mounting block displaceably mounted to the first track and a first gas detector mounted on the first mounting block. The apparatus further includes a displacement mechanism that displaces the first mounting block along the first track between: a first position located inside the cellar; and a second position located outside of the cellar. A related method includes: providing a first track; displaceably mounting a first mounting block to the first track; and mounting a first gas detector on the first mounting block. The method further includes displacing, via a first displacement mechanism, the first mounting block along the first track between: a first position located inside a cellar; and a second position located outside of the cellar.

11 Claims, 4 Drawing Sheets

(56) References Cited

U.S. PATENT DOCUMENTS

| | | | | |
|---|---|---|---|---|
| 2013/0270006 | A1* | 10/2013 | Selman | E21B 49/005<br>175/24 |
| 2023/0339675 | A1* | 10/2023 | Collins | B65D 90/10 |
| 2024/0310346 | A1* | 9/2024 | Miller | G01N 33/0063 |

FOREIGN PATENT DOCUMENTS

| | | | |
|---|---|---|---|
| CN | 216745970 | U | 6/2022 |
| CN | 217976315 | U | 12/2022 |

OTHER PUBLICATIONS

"Combustible Gas and Hydrogen Sulfide in Air Detection Systems", SAES-J-505; Engineering Standard; Jan. 31, 2005; pp. 1-16 (16 pages).

"1910.146—Permit-requried confined spaces", Accessed: Jul. 26, 2023; pp. 1-20; Retrieved from the Internet: URL: https://www.osha.gov/laws-regs/regulations/standardnumber/1910/1910.146.

* cited by examiner

MOVABLE MOUNT FOR WELL CELLAR GAS DETECTORS

BACKGROUND

Conventionally, many oil and gas wells are provided with a cellar, that is, a small underground room or space that provides space for equipment adjacent to a well. As a general protective measure, gas detectors may be provided in the cellar and can include a Lower Explosive Limit (LEL) gas detector and a hydrogen sulfide (H2S) gas detector.

Typically, personnel such as technicians may need to access the cellar on a regular basis, e.g., at least quarterly, to perform preventive maintenance on the detectors. Despite the safety measures normally in place, conventional practice nonetheless tends to require considerable preparation yet still exposes technicians to significant potential hazards such as gas leaks, a risk of slipping and falling, and wildlife infiltration. Rescue efforts in the event of a related emergency can often be time-consuming and complex.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to an apparatus for a cellar of a well. The apparatus includes a first track, a first mounting block displaceably mounted to the first track and a first gas detector mounted on the first mounting block. The apparatus further includes a displacement mechanism that displaces the first mounting block along the first track between: a first position located inside the cellar; and a second position located outside of the cellar.

In one aspect, embodiments disclosed herein relate to a method comprising: providing a first track; displaceably mounting a first mounting block to the first track; and mounting a first gas detector on the first mounting block. The method further includes displacing, via a first displacement mechanism, the first mounting block along the first track between: a first position located inside a cellar; and a second position located outside of the cellar.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Figure 1:
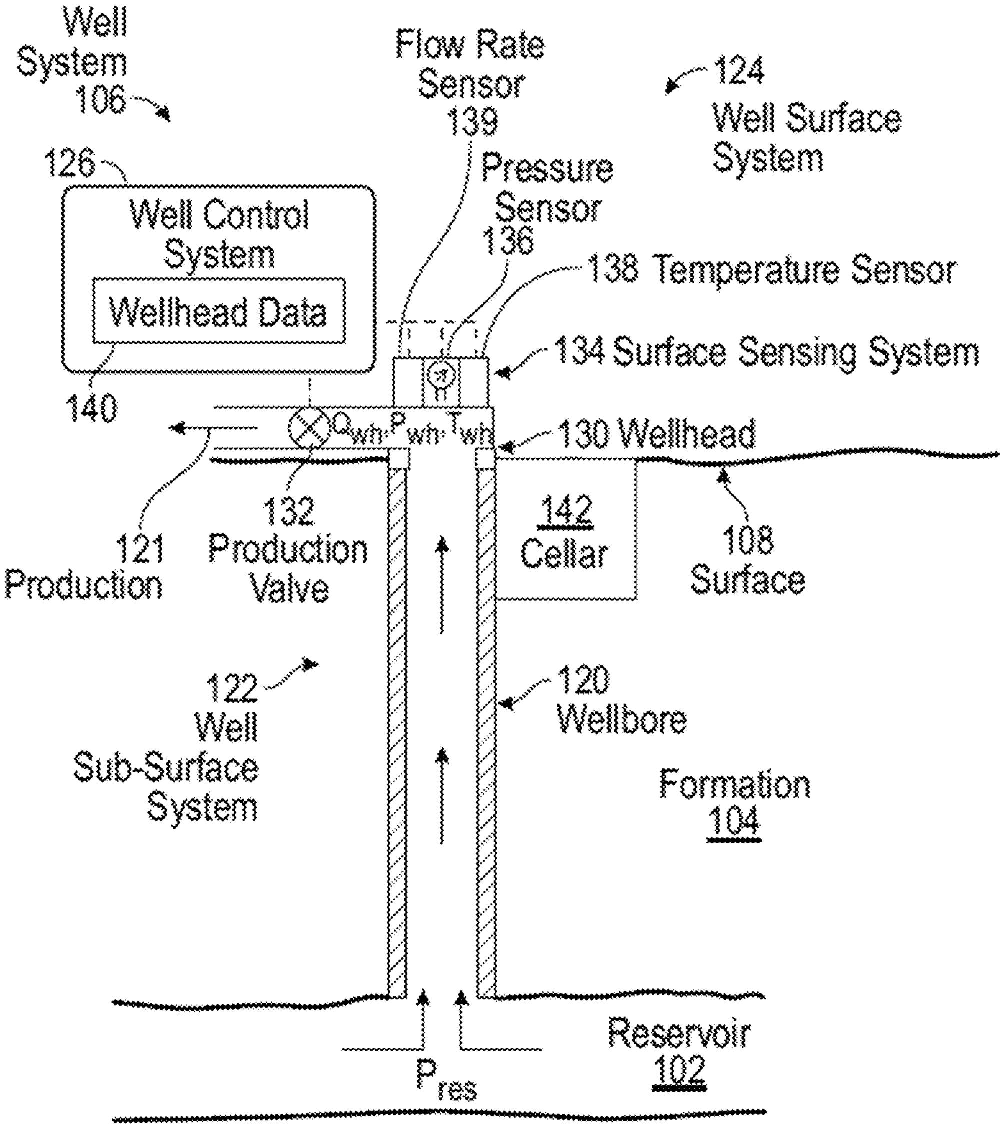
FIG. 1 schematically illustrates, in a cross-sectional elevational view, a wellbore and a well control system in accordance with one or more embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Broadly contemplated herein, in accordance with one or more embodiments, is a simplified mounting mechanism that permits personnel, in the course of preventative maintenance for a cellar at an oil or gas well, to retrieve one or more gas detectors from a position outside of the cellar. The mounting mechanism can thereby significantly mitigate a risk of sparking or any other possible source of ignition, and can meet strict industry requirements including the use of a vibration-free surface, and can be made from any of a great variety of non-metallic materials.

In accordance with one or more embodiments, gas detectors (such as LEL and H2S gas detectors) can be mounted on a movable mount that includes pulling cables or other pulley mechanics. Thus, personnel may retrieve the detectors from a position outside of or apart from the cellar, to safely perform any needed function checks or calibrations from such a position. Thus, any and all potential hazards normally associated with confined space entry (CSE) can be averted.

Turning now to the figures, to facilitate easier reference when describing FIGS. 1-4, reference numerals may be advanced by a multiple of 100 in indicating a similar or analogous component or element among FIGS. 1-4.

FIG. 1 schematically illustrates, in a cross-sectional elevational view, a wellbore and a well control system in accordance with one or more embodiments, at a hydrocarbon well. The well system 106 includes a wellbore 120, a well sub-surface system 122, a well surface system 124, and a well control system ("control system") 126. The control system 126 may control various operations of the well system 106, such as well production operations, well completion operations, well maintenance operations, and reservoir monitoring, assessment and development operations.

In accordance with one or more embodiments, the wellbore 120 includes a bore hole that extends from the terrestrial surface 108 into a target zone of the formation 104, such as the reservoir 102. An upper end of the wellbore 120, terminating at or near the surface 108, may be referred to as the "up-hole" end of the wellbore 120, and a lower end of the wellbore, terminating in the formation 104, may be referred to as the "down-hole" end of the wellbore 120. The wellbore 120 facilitates the circulation of drilling fluids during drilling operations, the flow of hydrocarbon production fluid ("production fluid") 121 (e.g., oil and gas) from the reservoir 102 to the surface 108 during production operations, the injection of substances (e.g., water) into the formation 104 or the reservoir 102 during injection operations, or the communication of monitoring devices (e.g., logging tools) into the formation 104 or the reservoir 102 during monitoring operations (e.g., during in situ logging operations).

In accordance with one or more embodiments, during operation of the well system 106, the control system 126 collects and records wellhead data 140 for the well system 106. The wellhead data 140 may include, for example, a record of measurements of wellhead pressure ($P_{wh}$) (e.g., including flowing wellhead pressure), wellhead temperature ($T_{wh}$) (e.g., including flowing wellhead temperature), wellhead production flow rate ($Q_{wh}$) over some or all of the life of the well 106, and water cut data. Such measurements may be recorded in real-time, to be available for review or use within seconds, minutes, or hours of the condition being sensed (e.g., within one hour). Such real-time data can help an operator of the well 106 to assess a relatively current state of the well system 106 and to make real-time decisions regarding development of the well system 106 and the reservoir 102, such as on-demand adjustments in regulation of production flow from the well. As will be discussed in greater detail below, a control system analogous to that indicated at 126 may also be used to obtain pressure measurements from different locations in a manner to control the opening and closing of an annulus relief line check valve.

In accordance with one or more embodiments, the well sub-surface system 122 includes a casing installed in the wellbore 120. For example, the wellbore 120 may have a cased portion and an uncased (or "open-hole") portion. The cased portion may include a portion of the wellbore having casing disposed therein. The uncased portion may include a portion of the wellbore not having casing disposed therein. In embodiments having a casing, the casing defines a central passage that provides a conduit for the transport of tools and substances through the wellbore 120. For example, the central passage may provide a conduit for lowering logging tools into the wellbore 120, a conduit for the flow of production fluid 121 (e.g., oil and gas) from the reservoir 102 to the surface 108, or a conduit for the flow of injection substances (e.g., water) from the surface 108 into the formation 104. The well sub-surface system 122 can include production tubing (not shown) installed in the wellbore 120. The production tubing may provide a conduit for the transport of tools and substances through the wellbore 120. The production tubing may, for example, be disposed inside casing. In such an embodiment, the production tubing may provide a conduit for some or all of the production fluid 121 (e.g., oil and gas) passing through the wellbore 120 and the casing.

In accordance with one or more embodiments, the well surface system 124 includes a wellhead 130. Wellhead 130 may include a rigid structure installed at the "up-hole" end of the wellbore 120, at or near where the wellbore 120 terminates at the Earth's surface 108. The wellhead 130 may include structures (called "wellhead casing hanger" for casing and "tubing hanger" for production tubing) for supporting (or "hanging") casing and production tubing extending into the wellbore 120. Production fluid 121 may flow through the wellhead 130, after exiting the wellbore 120 and the well sub-surface system 122, including, for example, the casing and the production tubing. The well surface system 124 may include flow regulating devices that are operable to control the flow of substances into and out of the wellbore 120. For example, the well surface system 124 may include one or more production valves 132 that are operable to control the flow of production fluid 121. For instance, a production valve 132 may be fully opened to enable unrestricted flow of production fluid 121 from the wellbore 120, the production valve 132 may be partially opened to partially restrict (or "throttle") the flow of production fluid 121 from the wellbore 120, and production valve 132 may be fully closed to fully restrict (or "block") the flow of production fluid 121 from the wellbore 120, and through the well surface system 124.

In accordance with one or more embodiments, the wellhead 130 includes a choke assembly (not shown). For example, the choke assembly may include hardware with functionality for opening and closing the fluid flow through pipes in the well system 106. Likewise, the choke assembly may include a pipe manifold that may lower the pressure of fluid traversing the wellhead 130. As such, the choke assembly may include a set of high-pressure valves (not shown) and one or two chokes (not shown). These chokes may be fixed or adjustable or a mix of both. Redundancy may be provided so that if one choke has to be taken out of service, the flow can be directed through another choke. In some embodiments, pressure valves and chokes are communicatively coupled to the well control system 126. Accordingly, a well control system 126 may obtain wellhead data regarding the choke assembly as well as transmit one or more commands to components within the choke assembly in order to adjust one or more choke assembly parameters.

In accordance with one or more embodiments, the well surface system 124 includes a surface sensing system 134. The surface sensing system 134 may include sensors for sensing characteristics of substances, including production fluid 121, passing through or otherwise located in the well surface system 124. The characteristics may include, for example, pressure, temperature and flow rate of production fluid 121 flowing through the wellhead 130, or other conduits of the well surface system 124, after exiting the wellbore 120.

In accordance with one or more embodiments, the surface sensing system 134 includes a surface pressure sensor 136 operable to sense the pressure of production fluid 121 flowing through the well surface system 124, after it exits the wellbore 120. The surface pressure sensor 136 may include, for example, a wellhead pressure sensor that senses a pressure of production fluid 121 flowing through or otherwise located in the wellhead 130. In some embodiments, the surface sensing system 134 includes a surface temperature sensor 138 operable to sense the temperature of production fluid 121 flowing through the well surface system 124, after it exits the wellbore 120. The surface temperature sensor 138 may include, for example, a wellhead temperature sensor that senses a temperature of production fluid 121 flowing through or otherwise located in the wellhead 130, referred to as "wellhead temperature" ($T_{wh}$). In some embodiments, the surface sensing system 134 includes a flow rate sensor 139 operable to sense the flow rate of production fluid 121 flowing through the well surface system 124, after it exits the wellbore 120. The flow rate sensor 139 may include hardware that senses a flow rate of production fluid 121 ($Q_{wh}$) passing through the wellhead 130.

In accordance with one or more embodiments, the well system 106 may be an oil or gas well system and the reservoir 102 may be an oil or gas reservoir. As noted heretofore, a cellar 142 may be provided, in the form of a small underground room or space just under the terrestrial surface 108, that provides space for equipment adjacent to the wellbore 120. One or more LEL detectors and one or more H2S detectors may be provided in the cellar.

Figure 2:
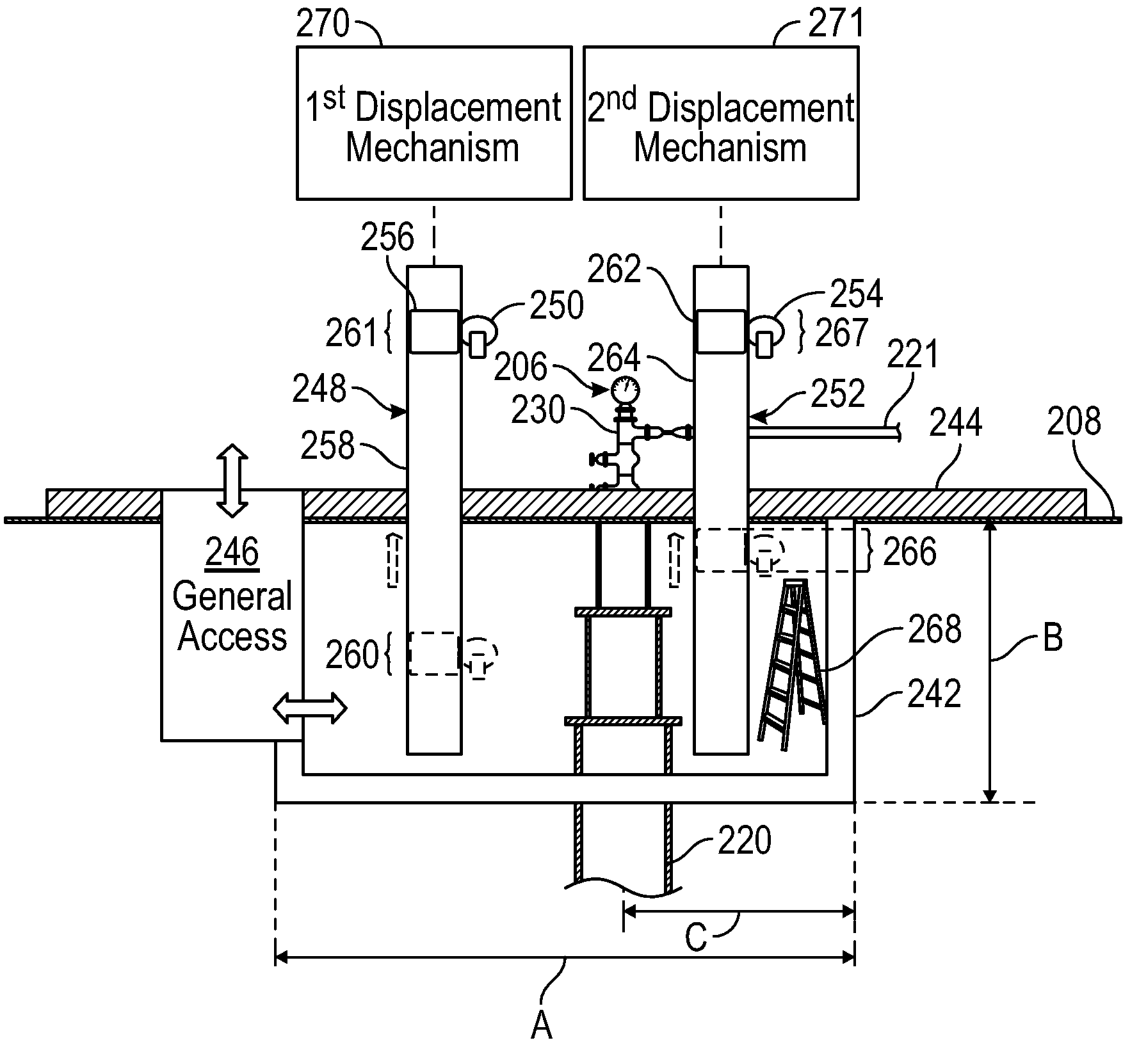
FIG. 2 schematically illustrates a cellar for an oil or gas well, in accordance with one or more embodiments.

In accordance with one or more embodiments, FIG. 2 schematically illustrates a cellar 242 for an oil or gas well. As shown, the cellar 242 may be located underground just beneath terrestrial surface 208 and a metal grating platform 244, adjacent to wellbore 220. The cellar 242, which may also be referred to as an "oil/gas wellhead cellar", may include walls formed from concrete. In accordance with one or more variants, the cellar 242 may be at a location that is not fully underground (i.e., beneath terrestrial surface 208), but instead is partially underground or fully "above-ground" (i.e., above terrestrial surface 208).

In accordance with one or more embodiments, the well system 206 may include a wellhead 230, with a production line 221 leading away from the wellhead 230. Typically, general access 246 to the cellar may be provided in the form of a stairwell or ladder. By way of sample dimensions in accordance with an illustrative example, the cellar 242 may have an overall length A of about 6.71 meters and overall height B of about 4.67 meters. The distance C, as shown, from a wall of cellar 242 to a centerline of the wellhead 230 and wellbore 220 may be about 2.74 meters. A width of the cellar, measured in a perpendicular direction with respect to the plane of the figure, may be about 3.96 meters. Additionally, the centerline of the wellhead 230 and wellbore 220 may be located about halfway into this width of the cellar. A person of ordinary skill in the art will appreciate that these dimensions of the cellar 242 are provided as examples, and that the dimensions may vary based on, for example, a type of well, a location of a well, a formation in which a wellbore is formed, size of equipment to be located in the cellar, etc.

In accordance with one or more embodiments, one or more movable mounts may be provided to facilitate ready removal of gas detectors from cellar 242, for purposes of preventative maintenance. Thus, as shown in FIG. 2, two such movable mounts are provided, wherein a first movable mount 248 is configured for mounting an H2S detector 250 and a second movable mount 252 is configured for mounting an LEL detector 254. Although FIG. 2 shows the movable mounts 248, 252 having a H2S detector 250 and an LEL detector 254 mounted thereto, respectively, a person of ordinary skill in the art will appreciate that other detectors may be coupled to movable mounts without departing from the scope of embodiments disclosed herein.

In accordance with one or more embodiments, first movable mount 248 may include a mounting block 256 that is displaceably mounted on a first track 258 that is oriented generally vertically. Mounting block 256 may be formed from a low-friction, non-sparking material such as any of a great variety of hard, durable non-metallic materials. Illustrative and non-restrictive examples of such materials include polytetrafluoroethylene (PTFE), nylon, and polycarbonate. Consequently, the mounting block 256 may engage and be displaceable along the first track 258 in essentially any suitable manner that resists sparking or excessive friction. Thus, by way of an illustrative and non-restrictive example, the mounting block 256 may be embodied as a monolithic block component (e.g., a component without supplementary elements for facilitating displacement such as wheels or sliding pads) while the first track 258 may be embodied by two parallel and mutually opposing C-channels formed from galvanized steel. The mounting block (or monolithic block component) 256 may then extend laterally between the two C-channels such that two opposite longitudinal sides of the mounting block 256 are accommodated within the mutually opposing C-channels, such that the C-channels guide longitudinal sliding displacement of the mounting block 256. However, in accordance with one or more variants, the mounting block 256 may alternatively include suitable wheels or low-friction sliding pads that engage with one or more portions of first track 258.

In accordance with one or more embodiments, via a first displacement mechanism 270, the mounting block 256 and H2S detector 250 may selectively be displaced by personnel in a generally upward direction (as shown via the adjacent dotted arrow) from a first position 260 within the cellar 242 to a second position 261 outside of the cellar 242 and above the terrestrial surface 208. By way of illustrative and non-restrictive example, the first displacement mechanism 270 may be embodied by a system that includes one or more ropes or cables and one or more pulleys. In accordance with one or more variants, a simple winding system may be employed, wherein no pulleys are involved but one or more ropes or cables are wound about a shaft and, upon rotation of the shaft, may displace the mounting block 256 and H2S detector 250 in a direction toward or away from second position 261. In accordance with one or more variants, any of a great variety of other arrangements may be employed for first displacement mechanism 270, including (but not limited to) a hydraulically or mechanically operated shaft that selectively displaces the mounting block 256 and H2S detector in a direction toward or away from second position 261.

Thus, once displaced by first displacement mechanism 270 to a position outside of the cellar 242 (e.g., to the second position 261), the H2S detector 250 may safely be checked and calibrated for preventative maintenance or other purposes. Likewise, the block 256 itself may also be checked and maintained as appropriate once outside of the cellar 242.

In similar fashion as noted above, and in accordance with one or more embodiments, second movable mount 252 may include a mounting block 262 that is displaceably mounted with respect to a second track 264 oriented generally vertically. The mounting block 262 and second track 264 may be constructed and configured similarly to the mounting block 256 and first track 258 discussed above, respectively.

In accordance with one or more embodiments, again, via a second displacement mechanism 271, the mounting block 262 and LEL detector 254 may selectively be displaced by personnel in a generally upward direction (as shown via the adjacent dotted arrow) from a third position 266 within the cellar 242 to a fourth position 267 outside of the cellar 242 and above the terrestrial surface 208. By way of illustrative and non-restrictive example, the second displacement mechanism 271 may be embodied by a system that includes one or more ropes or cables and one or more pulleys, or essentially in any manner similar or analogous to that described above for first displacement mechanism 270. Thus, in similar manner as discussed above and once outside of the cellar 242 (e.g., in the fourth position 267), the LEL detector 250 may then be safely checked and calibrated for preventative maintenance or other purposes, along with the block 262 itself.

In accordance with one or more embodiments, it can also be appreciated that the LEL detector 254, in particular, may normally be located at a position within the cellar 242 (e.g., third position 266) that is generally higher (i.e., closer to the terrestrial surface 208) than other detectors or instruments within cellar 242 (e.g., at first position 260), and may conventionally need to be accessed by a stand-alone ladder 268. Thus, by safely removing the LEL detector 254 to the fourth position 267 outside of cellar 242, an additional risk of personal injury is also mitigated with no need to access stand-alone ladder 268. By way of an illustrative and non-restrictive example, first position 260 may be about 1.0 meter above the floor of cellar 242 and third position 266 may be about 1.5 to 1.8 meters, or even more, above the floor of cellar 242.

Figure 3:
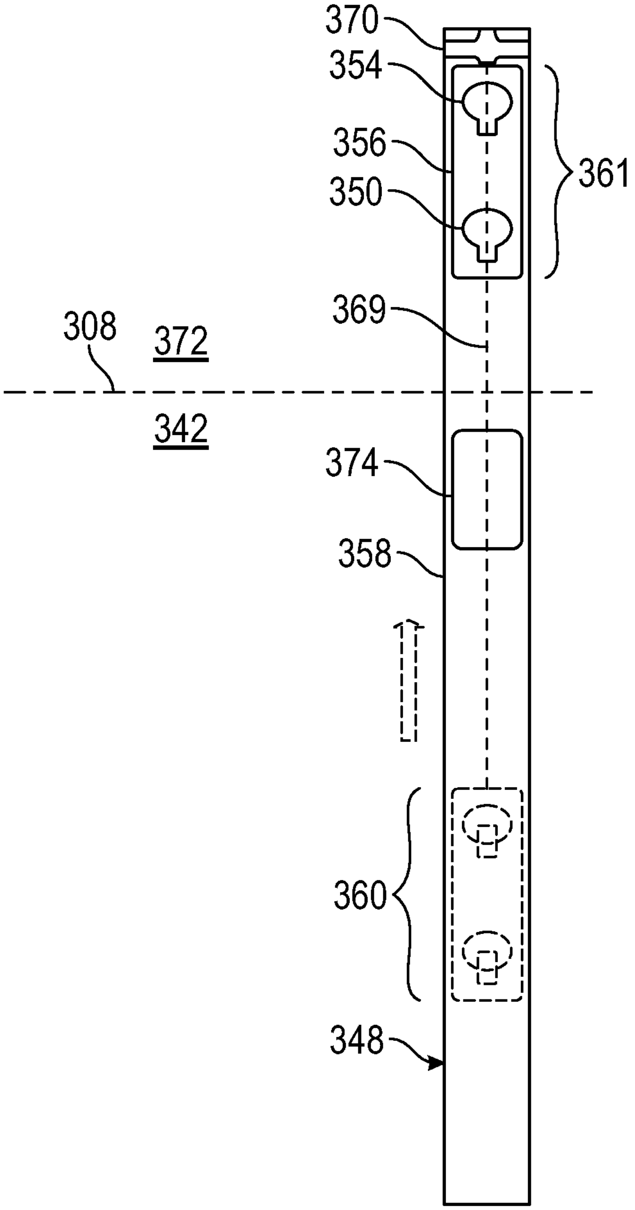
FIG. 3 is a schematic front elevational view of a movable mount that includes two gas detectors, in accordance with one or more embodiments.

In accordance with one or more embodiments, FIG. 3 provides a schematic front elevational view of a movable mount 348 that includes two gas detectors. As shown, an LEL detector 354 and H2S detector 350 may be commonly mounted on mounting block 356 that displaces along a track 358. The mounting block 356 may be constructed and configured similarly to the mounting blocks 256 and 262 discussed above, and the track 358 may be configured similarly to the tracks 258 and 264 discussed above. One or more ropes 369 mounted on a pulley (or pulley system) 370 and coupled to the mounting block 356 then permit mounting block 356 to be pulled upwardly (as indicated by the upward dotted arrow) from a first position 360 within cellar 342 to a second position 361 outside of the cellar 342 and in a "safe" room or space 372, e.g., above terrestrial surface 308. A suitable counterweight 374 may also be attached to the one or more ropes 369 if deemed to be warranted. Here, as well, personnel in the "safe" room or space 372 may perform preventative maintenance on the detectors 354/350 as needed.

In accordance with one or more embodiments, the mounting block 356 may be of sufficient length (e.g., in a generally vertical direction) such that, when in first position 360, the detectors 354 and 350 are positioned above the floor (or a lower grating platform) of cellar 342 at similar heights as those discussed above for detectors 254 and 250. Thus, when mounting block 356 is in first position 360, H2S detector 350 may be positioned at about 1.0 meter above the floor of cellar 242 and LEL detector 254 may be positioned at about 1.5 to 1.8 meters, or even more, above the floor of cellar 242. In other embodiments, the mounting block 356 may comprise two separate mounting blocks attached to or mounted on the one or more ropes 369 and separated a distance from each other axially along the one or more ropes 369. Each detector 354, 350 may then be mounted to one of the separate blocks. The axial distance between the two separate mounting blocks and therefore the distance between the detectors 354, 350, may therefore be adjustable. Generally, it should be understood that these dimensions are provided merely by way of illustrative and non-restrictive examples. Thus, in practice, the dimensions may differ on the basis of individual cellar design, or of requirements related to ergonomics in connection with access for preventative maintenance.

Figure 4:
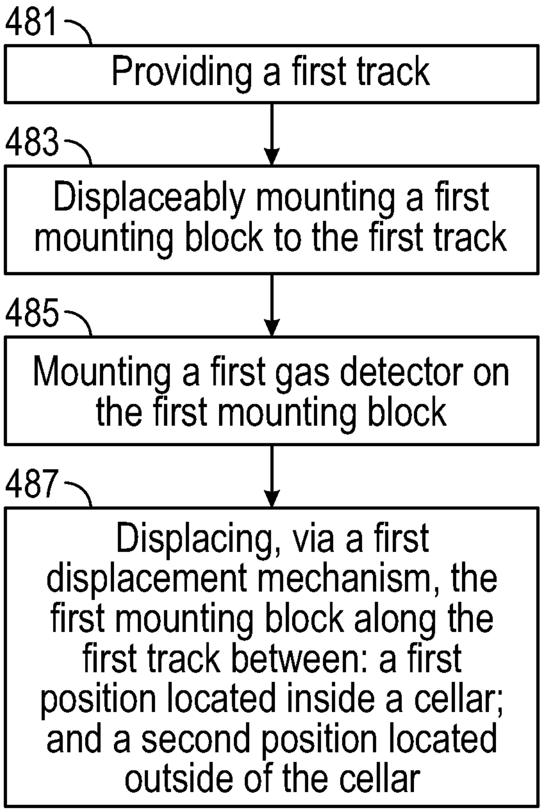
FIG. 4 shows a flowchart of a method, in accordance with one or more embodiments.

FIG. 4 shows a flowchart of a method, as a general overview of steps that may be carried out in accordance with one or more embodiments described or contemplated herein. Specifically, FIG. 4 describes a method of providing one or more movable mounts for a cellar. One or more blocks in FIG. 4 may be performed using one or more components as described in FIGS. 1-3. While the various blocks in FIG. 4 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

As such, in accordance with one or more embodiments, a first track is provided (481). In accordance with merely illustrative examples, this may correspond to provision of the first track 258 or second track 264 shown in FIG. 2 or track 358 shown in FIG. 3. A first mounting block is displaceably mounted to the first track (483). In accordance with merely illustrative examples, this may correspond to displaceably mounting the mounting block 256, 262 or mounting block 356 shown in FIG. 2 or 3, respectively. A first gas detector is mounted on the first mounting block (485). In accordance with merely illustrative examples, this may correspond to mounting the gas detector 250 or mounting both of the gas detectors 350/354, as shown in FIG. 2 or 3, respectively. Via a first displacement mechanism, the first mounting block is displaced along the first track between: a first position located inside a cellar; and a second position located outside of the cellar (487). In accordance with illustrative examples, the cellar may correspond to that indicated at 242 in FIG. 2, and the first and second positions may correspond to those indicated at 260 and 261, respectively in FIG. 2. Alternatively, the cellar may correspond to that indicated at 342 in FIG. 3, and the first and second positions may correspond to those indicated at 360 and 361, respectively in FIG. 3. Additionally, the first displacement mechanism may correspond to that indicated at 270, 271 in FIG. 2 or to the pulley system 370 and one or more ropes 369 shown in FIG. 3.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed:

1. An apparatus for a cellar of a well, said apparatus comprising:
- a first track;
- a first mounting block displaceably mounted to the first track;
- a first gas detector mounted on the first mounting block and a second gas detector mounted on the first mounting block; and
- a first displacement mechanism that displaces the first mounting block along the first track between:
  - a first position located inside the cellar and below a terrestrial surface; and
  - a second position located outside of the cellar and above the terrestrial surface;
- wherein the first gas detector is a Lower Explosive Limit (LEL) gas detector and the second gas detector is a hydrogen sulfide (H2S) gas detector.

2. The apparatus according to claim 1, wherein the cellar is adjacent to an oil well or gas well.

3. The apparatus according to claim 1, further comprising:
- a second track;
- a second mounting block displaceably mounted with respect to the second track,
- wherein the second gas detector is mounted on the second mounting block; and
- a second displacement mechanism that displaces the second mounting block along the second track between:
  - a third position located inside the cellar and below the terrestrial surface; and
  - a fourth position located outside of the cellar and above the terrestrial surface.

4. The apparatus according to claim 3, wherein the third position is at a higher position in the cellar than the first position.

5. The apparatus according to claim 1, wherein the first displacement mechanism comprises one or more ropes mounted on a pulley system.

6. The apparatus according to claim 1, wherein the first mounting block is formed from a non-sparking material.

7. The apparatus according to claim 1, wherein the first mounting block comprises a monolithic block component, and the first track guides sliding displacement of the monolithic block component.

8. A method comprising:
providing a first track;
displaceably mounting a first mounting block to the first track;
mounting a first gas detector on the first mounting block and mounting a second gas detector mounted on the first mounting block; and
displacing, via a first displacement mechanism, the first mounting block along the first track between:
a first position located inside the cellar and below a terrestrial surface; and
a second position located outside of the cellar and above the terrestrial surface
wherein the first gas detector is a Lower Explosive Limit (LEL) gas detector and the second gas detector is a hydrogen sulfide (H2S) gas detector.

9. The method according to claim 8, wherein the cellar is adjacent to an oil well or gas well.

10. The method according to claim 8, further comprising:
providing a second track;
displaceably mounting a second mounting block to the second track;
mounting the second gas detector on the second mounting block; and
displacing, via a second displacement mechanism, the second mounting block along the second track between:
a third position located inside the cellar and below the terrestrial surface; and
a fourth position located outside of the cellar and above the terrestrial surface.

11. The method according to claim 10, wherein the third position is at a higher position in the cellar than the first position.

* * * * *